United States Patent [19]

Hagenbach et al.

[11] Patent Number: 4,634,708

[45] Date of Patent: Jan. 6, 1987

[54] INDOLOPHENANTHRIDINES USEFUL AS DOPAMINERGIC AND ANALGESIC AGENTS

[75] Inventors: Alexander Hagenbach, Pfeffingen; Max P. Seiler, Basel; Hans J. Wüthrich, Kehrsatz, all of Switzerland

[73] Assignee: Sandoz Ltd., Basel, Switzerland

[21] Appl. No.: 695,191

[22] Filed: Jan. 25, 1985

[30] Foreign Application Priority Data

Jan. 25, 1984 [DE] Fed. Rep. of Germany ....... 3402392

[51] Int. Cl.$^4$ .................. A61K 31/475; C07D 471/06
[52] U.S. Cl. .................................... 514/280; 546/49; 546/56; 546/57; 548/436
[58] Field of Search ....................... 546/49, 56, 67, 57; 514/280

[56] References Cited

U.S. PATENT DOCUMENTS

| | | | |
|---|---|---|---|
| Re. 31,194 | 3/1983 | Horwell et al. | 546/68 |
| 4,075,213 | 2/1978 | Kornfeld et al. | 546/67 |
| 4,202,979 | 5/1980 | Kornfeld et al. | 546/67 |

*Primary Examiner*—Donald G. Daus
*Assistant Examiner*—Diana G. Rivers
*Attorney, Agent, or Firm*—Gerald D. Sharkin; Robert S. Honor; Thomas O. McGovern

[57] ABSTRACT

4,6,6a,7,8,12b-hexahydro-indolo[4,3-ab]phenanthridines are useful as dopaminergic and analgesic agents.

17 Claims, No Drawings

INDOLOPHENANTHRIDINES USEFUL AS DOPAMINERGIC AND ANALGESIC AGENTS

The present invention relates to indolophenanthridines.

The invention provides 4,6,6a,7,8,12b-hexahydroindolo[4,3-ab]phenanthridines in free base or acid addition salt form. No such compound has been disclosed or suggested hitherto in the literature. These compounds, hereinafter referred to as novel compounds, have the following structure:

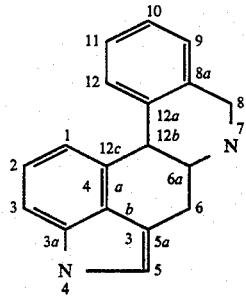

A

This basic structure may be substituted by inert, pharmacologically acceptable groups. Examples of such groups are well known to the skilled man. In particular the 4, 5, 7, 9, 10, 11 and 12 positions may be substituted. The following substituents may be present:

In 4 and 7 position: optionally substituted, lower alkyl.

In 5 position: methyl or halogen.

In 9, 10, 11 and 12 position: lower alkyl, lower alkoxy, hydroxy, halogen or trifluoromethyl.

The new compounds possess two asymmetrical carbon atoms in positions 6a and 12b. They may therefor appear in racemic or optically active forms. The invention relates to both the racemates and the optically active forms.

The new compounds may be present in free base form or as acid addition salts. The invention relates to both the free bases and the addition salt forms. Examples of suitable pharmaceutically acceptable acid addition salt forms are the hydrochlorides, hydrobromides and hydrogen fumarates.

The invention relates in particular to compounds of formula I

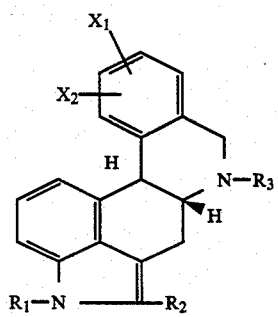

I wherein

R₁ and R₃ independently are hydrogen, (C₁₋₄)alkyl, (C₃₋₅)alkenyl wherein the double bond is not adjacent to the nitrogen atom, (C₃₋₆)cycloalkyl(C₁₋₃)alkyl, phenyl(C₁₋₃)alkyl optionally substituted in the phenyl ring by (C₁₋₄)alkyl, (C₁₋₄)alkoxy, hydroxy or halogen, or 2- or 3-furyl(C₁₋₃)alkyl, R₂ is hydrogen, chlorine, bromine or methyl, X₁ and X₂ independently are hydrogen, (C₁₋₄)alkyl, (C₁₋₄)alkoxy, hydroxy, halogen or trifluoromethyl, in free base or acid addition salt form.

Any alkyl or alkoxy preferably has one or two carbon atoms and especially one carbon atom.

Any halogen has an atomic number from 9 to 53. Preferred halogens are bromine and chlorine. When a phenyl(C₁₋₃)alkyl is substituted, it is conveniently substituted by up to 3 substituents.

The following significances and their combinations are preferred:

R₁ is hydrogen or (C₁₋₄)alkyl,

R₃ is hydrogen, (C₁₋₄)alkyl, benzyl optionally mono substituted by (C₁₋₄)alkoxy or 2-furylmethyl, and/or X₂ is hydrogen.

In a group of compounds of formula I,

R₁ and R₃ independently are hydrogen, (C₁₋₄)alkyl, (C₃₋₅)alkenyl wherein the double bond is not adjacent to the nitrogen atom, (C₃₋₆)cycloalkyl(C₁₋₃)alkyl, phenyl(C₁₋₃)alkyl optionally monosubstituted by methyl, methoxy, hydroxy or halogen, or 2-or 3-furyl(C₁₋₃)alkyl, R₂ is hydrogen, chlorine, bromine or methyl, X₁ and X₂ independently are hydrogen, (C₁₋₄)alkyl, (C₁₋₄)alkoxy, hydroxy, halogen or trifluormethyl.

The present invention also provides a process for the production of a 4,6,6a,7,8,12b-hexahydro-indolo[4,3-ab]phenanthridine in free base or acid addition salt form, which comprises oxidizing in 5,5a position a corresponding 4,5,5a,6,6a,7,8,12b-octahydroindolo[4,3-ab]phenanthridine, and optionally converting the thus obtained indolophenanthridine into the desired indolophenanthridine and recovering the resultant indolophenanthridine in free base or acid addition salt form.

The invention provides in particular a process for the production of a compound of formula I or an acid addition salt thereof, which includes the step of oxidizing in 5,5a position of the indolophenanthridine ring an appropriate compound of formula II

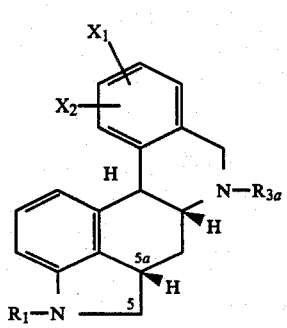

II wherein R₁, X₁ and X₂ are as defined above and R₃ₐ is as defined for R₃ but not hydrogen, and obtaining a compound of formula I in free base or acid addition salt form. The resulting product of formula Ia

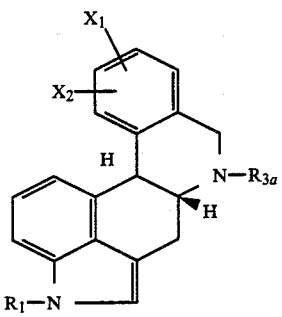

wherein $R_1$, $R_{3a}$, $X_1$ and $X_2$ are as defined above, may be converted into a further compound of formula I, e.g. by alkylation, dealkylation and halogenation.

Thus the resulting compounds of formula I can be produced from the compounds of formula Ia by using the following steps alone or in combination:

(a) for the production of a compound of formula Ib

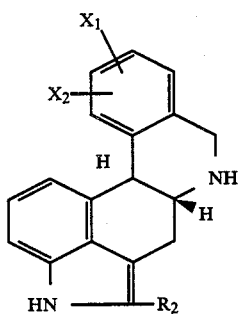

wherein $R_2$, $X_1$ and $X_2$ are as defined above, dealkylating in position an appropriate compound of formula I′

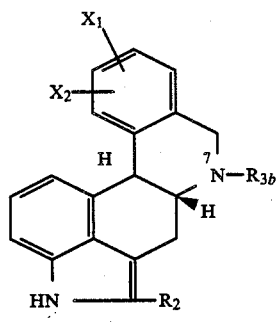

wherein $R_2$, $X_1$ and $X_2$ are as defined above and $R_{3b}$ is methyl or benzyl;

(b) for the production of a compound of formula Ic

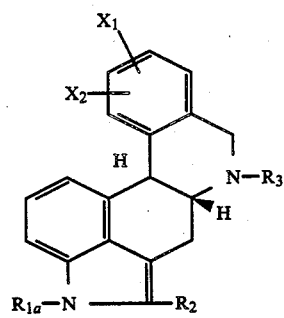

wherein $R_2$, $R_3$, $X_1$ and $X_2$ are as defined above, and $R_{1a}$ is as defined for R, but not hydrogen, alkylating, which also includes alkenylating, cycloalkylalkylating and phenylalkylating, in the 4 position an appropriate compound of formula I″

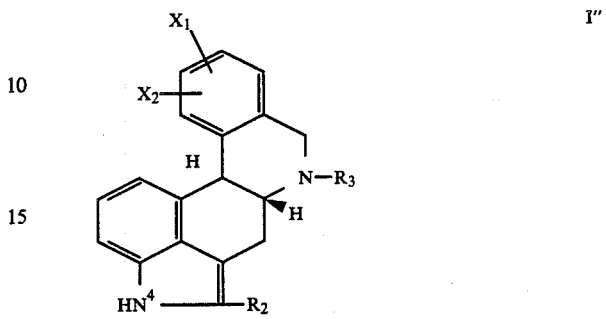

wherein $R_2$, $R_3$, $X_1$ and $X_2$ are as defined above;

(c) for the production of a compound of formula Id

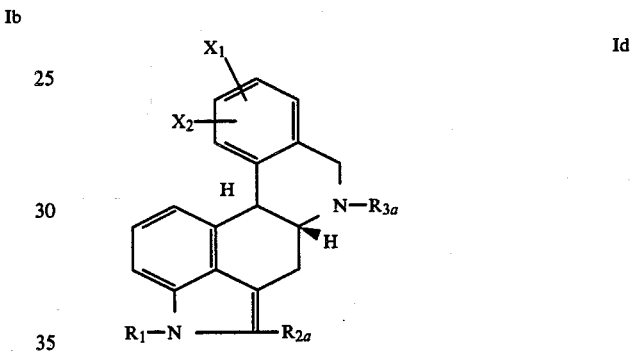

wherein $R_1$, $R_{3a}$, $X_1$ and $X_2$ are as defined above and $R_{2a}$ is chlorine, bromine or methyl, methylating or halogenating in 5 position an appropriate compound of formula Ia as defined above.

The oxidation of the compounds of formula II as well as processes (a), (b) and (c) can be effected according to conventional methods. These methods are known in particular from the chemistry of the ergot alkaloids, since the new compounds present the structure of an ergoline which is anellated in 8,9 position with a phenyl ring.

The oxidation of the compounds of formula II is carried out for example with $MnO_2$ as a mild oxidation agent.

The dealkylation according to (b) takes place in particular by hydrogenolytic debenzylation or by demethylation with BrCN and $K_2CO_3$ in $CHCl_3$, followed by reduction with acetic acid and Zn in water.

The alkylation of process (b) can take place selectively in known manner, that is without additional alkylation of the 7-N-atom, by making use of the strong azide character of the H-atom on $N_4$. For this, the starting compound of formula I″ is reacted with an equivalent of a strong base, especially NaH, thus forming the mono-sodium salt of this starting product (salt formation only on the 4-N-atom). The salt can then be readily reacted with the equivalent quantity of an alkyl halide, thus effecting selective alkylation of the 4-N-atom. Methyl iodide can be used for the methylation.

The halogenation of process (c) may take place e.g. for the introduction of a bromine atom with N- bromosuccinimide and for introduction of a chlorine atome with SO₂Cl₂ and boron trifluoride etherate.

For the methylation, the starting material of formula Ia may be reacted with dithiolane and SO₂Cl₂ and subsequently desulphurised with Raney-Ni.

The starting products which are used for the above described processes comprise various 6a,12b-trans-stereoisomers. Each of the above described processes may be carried out using the starting products in the form of the individual optically active isomers or isomer mixtures, especially the racemates, and they then lead to the corresponding end products.

The racemates can be split into their individual optically active components, using known methods e.g. via appropriate acid addition salt formation with optically active acids e.g. (+)- or (−)-mandelic acid, and fractional crystallisation of the diastereoisomeric acid addition salts.

The novel compounds can be isolated in free form or in acid addition salt form using known methods.

The starting products of formula II may be produced by reducing a compound of formula III

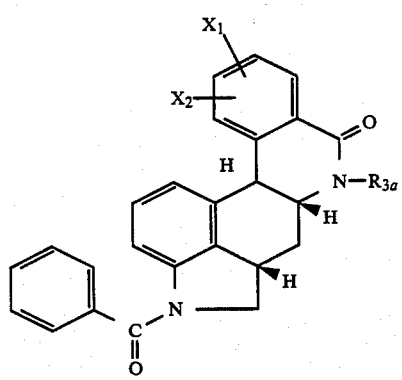

wherein $R_{3a}$, $X_1$ and $X_2$ are as defined above, in conventional manner, e.g. with LiAlH₄ or B₂H₆, and optionally alkylating the resulting compound in 4 position.

A compound of formula III may be obtained by photocyclising a compound of formula IV

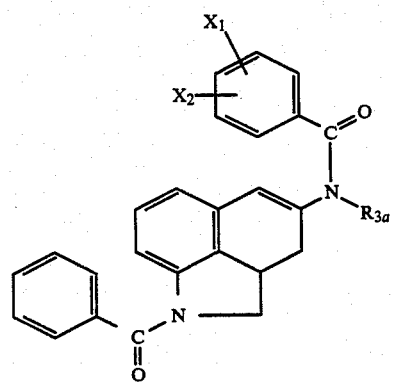

wherein $R_{3a}$, $X_1$ and $X_2$ are as defined above.

A compound of formula IV may for example be produced by reacting the compound of formula V

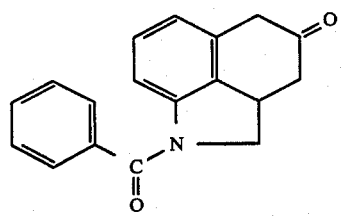

with a compound of formula VI

$$H_2N\text{---}R_{3a} \qquad VI$$

wherein $R_{3a}$ is as defined above, and subsequently a compound of formula VII

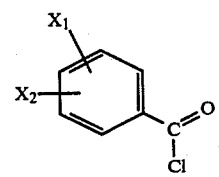

wherein $X_1$ and $X_2$ are as defined above, in conventional manner.

The invention also comprises the starting compounds of formulae II, III and IV as defined above per se.

Insofar as the preparation of the starting materials is not particularly described, these are known or may be prepared in conventional manner.

The 4,6,6a,7,8,12b-hexahydro-indolo[4,3-ab]phenanthridines and their pharmaceutically acceptable acid addition salts, hereinafter referred to as the compounds according to the invention, are novel and exhibit pharmacological activity and may therefore be used as pharmaceuticals.

They possess dopamine-receptor stimulating activity on the cardiovascular system, which is demonstated by the way in which they reduce blood pressure and lessen vascular resistance of the upper mesenteric artery in the anaesthetised dog [B. J. Clark, Postgrad. Med. J. 57 (Suppl. 1) 45–54].

Dogs which have been anaesthetised with chloralose and urethane are used for this test. The blood pressure is measured using a catheter in the femoral artery and the flow of blood into the upper mesenteric artery is measured using an electromagnetic blood-flow probe.

The compounds according to the invention bring about a reduction in blood pressure and a reduction in resistance in the mesenteric arteries at a dosage of between 100 and 1000 μg/kg.

The compounds according to the invention are therefore useful as dopamine receptor stimulants, e.g. both in the treatment of congestive cardiac insufficiency and of hypertension, or of renal failure with reduced urine excretion.

In this application, the dosage depends of course on the compound specifically used, the type of administration, the condition of the patient and the desired effect. In general however, satisfactory results are obtained upon administering a daily dose of approximately 4 to 20 mg/kg body weight, conveniently administered 2 to 4 times daily in divided doses or in sustained release form.

For larger mammals, the daily dosage is about 200 to 1000 mg; conveniently obtainable forms of dosage which are suitable for oral administration comprise about 50 to 300 mg of the compounds according to the invention, admixed with a pharmaceutically acceptable diluent or carrier.

In particular, the compounds according to the invention also show dopaminergic activity in vivo on the central nervous system, which is demonstrated by contralateral rotation upon administering doses of 1 to 10 mg/kg p.o. or 0.3 mg/kg s.c. to rats in which unilateral lesion of the nigro-neostriatal dopamine tract has been brought about by a 6-hydroxy-dopamine injection [U. Ungerstedt, Acta physiol. scand. Suppl. 367, 69–93 (1973)].

Similarly, the compounds according to the invention show stereotypy in the apomorphine-stereotypy test, upon administering quantities of approximately 30 mg/kg p.o.

In vitro, the compounds according to the invention stimulate dopamine-sensitive adenyl cyclase in the striatum homogenate of the rat, but are not acquainted with the electrically produced release of acetylcholine from striatum slices of the rat (tests according to Eur. J. Pharmacol. 95, 101).

The compounds according to the invention are therefore useful especially as selective dopaminergic active materials, e.g. for the treatment of Parkinson's disease.

For the treatment of Parkinson's disease, the dosage depends of course on the compound specifically used, the type of administration, the condition of the patient and the desired effect. In general however, satisfactory results are obtained upon administering approximately 0.02 to 3 mg/kg body weight, conveniently administered 2 to 4 times daily in part doses or in sustained release form.

For larger mammals, the daily dosage is approximately 1 to 100 mg, and conveniently obtainable forms of dosage which are suitable for oral administration comprise approximately 0.25 to 50 mg of the compounds according to the invention in free form or in pharmaceutically acceptable salt form, mixed with a pharmaceutically acceptable diluent or carrier.

Furthermore the compounds according to the invention possess analgesic activity, which is demonstrated for example in the hot plate test in mice [method according to Eddy and Leimbach, J. Pharmac. Exp. 107, 385 (1953)]upon administering doses of 10 to 100 mg/kg p.o., in the arthritis pain test in the rat [based on the method of A. W. Pircio et al., Eur. J. Pharmacol. 31, 207–215 (1975)]upon administering doses of 5 to 50 mg/kg p.o. and in the shock titration study in the rhesus monkey [based on the methods described by J. J. Boren et al. in Amer. J. Physiol. 201, 429 (1961), E. D. Weitzman et al. in Neurology 12, 264 (1962) and B. Weiss et al. in J. Pharmacol. Exp. Ther. 131, 120 (1961) and 143, 169 (1964)]at dosages of from 5 to 50 mg/kg p.o.

The compounds according to the invention are therefore useful as analgesic agents, e.g. in the treatment of pain.

For this use the dosage depends of course on the compound specifically used, the type of administration, the condition of the patient and the desired effect. In general, however, satisfactory results are obtained upon administering approximately 0.3 to 50 mg/kg body weight, conveniently administered in divided doses 2 to 4 times daily or in sustained release form. For larger mammals the daily dosage is approximately 50 to 150 mg. Suitable dosage forms e.g. for oral administration contain from about 10 to 75 mg of a compound according to the invention, together with a pharmaceutically acceptable diluent or carrier therefor.

The compounds according to the invention may be administered in similar manner to known standards for use in these utilities, for example bromocryptine for the treatment of Parkinson's disease which is the preferred indication. The suitable daily dosage for a particular compound will depend on a number of factors such as its relative potency of activity. It has for example be determined that the preferred compound of this invention which is the compound of example 2 induces about 2840 rotations in the above Ungerstedt model at a dose of 10 mg/kg p.o. as compared to about 1600 rotations for bromocryptine at a dose of 20 mg/kg p.o. It is therefore indicated that this compound may be administered at similar or lower dosages than conventionally employed for bromocryptine, e.g. about 10 mg per day.

Additionally for the analgesic indication, the compound of example 2 has an $ED_{50}$ of 37 mg/kg p.o. in the hot plate test ($ED_{50}$ of paracetamol in same test: 367 mg/kg p.o.) and an $ED_{50}$ of 20 mg/kg p.o. in the arthritis pain test ($ED_{50}$ of paracetamol in same test: 142 mg/kg p.o.). It is therefore indicated that this compound may be administered at about 5 to 10 times lower dosages than conventionally employed for the standard paracetamol, e.g. at 50 to 150 mg.

The present invention accordingly provides a compound according to the invention for use as a pharmaceutical, particularly for use in the treatment of Parkinson's disease, congestive cardiac insufficiency, hypertension, renal failure with reduced urine excretion and pain.

The compounds according to the invention may be administered in free base form or in pharmaceutically acceptable acid addition salt form. Such salts exhibit the same order of activity as the free bases. The present invention accordingly also provides a pharmaceutical composition comprising a compound according to the invention in association with a pharmaceutical carrier or diluent. Such compositions may be formulated in conventional manner. The compounds may be administered by any conventional route, in particular enterally, preferably orally, e.g., in the form of tablets or capsules, or parenterally, e.g., in the form of injectable solutions or suspensions.

The preferred compound is the title compound of Example 2.

In the following examples all temperatures are in degrees Centigrade and are uncorrected.

Example 1:
trans-4,6,6a,7,8,12b-hexahydro-7-methylindolo[4,3-ab]phenanthridine (a)

1,N-dibenzoyl-4-methylamino-1,2,2a,3-tetrahydrobenz[c,d]indole 30 g of 1-benzoyl-1,2,2a,3,4,5-hexahydro-4-ketobenz[c,d]indole are suspended in 1200 ml of diethylether together with 1.5 g of an acidic montmorillonite catalyst. Methylamine is passed into the stirred suspension at room temperature, any escaping methylamine is recondensed in a cooler coated with dry ice and is passed back into the reaction solution. During the course of the reaction, dissolving and reprecipitation take place, and the reaction is followed using thin-layer chromatography. When the reaction has ended, the excess methylamine is removed by bubbling nitrogen through the reaction solution, and the resultant deposit, the resultant crude enamine, is filtered off, dissolved in 600 ml of methylene chloride and filtered until clear. The filtrate is cooled to 0° and mixed with 14.6 ml of triethylamine. 12.4 ml of benzoyl chloride are added to this solution in drops at 0° whilst stirring. After this addition, the cooling is stopped, and the solution is stirred for a further 14 hours at room temperature. The reaction solution is subsequently extracted with 2N aqueous hydrochloric acid, followed by 2N ammonia solution, the combined organic phases are washed with salt solution, dried over magnesium sulphate, filtered and concentrated. The crude product is obtained as a yellow oil, which is further processed in this form.

(b)
(5aR*,6aS*,12bS*)-4-benzyol-4,5,5a,6,6a,7,8,12b-octahydro-8-keto-7-methylindolo[4,3-ab]phenanthridine 40 g of I,N-dibenzoyl-4-methylamino-1,2,2a,3-tetrahydrobenz[c,d]indole are dissolved in 2 liters of acetone, and irradiated with a high pressure quartz lamp (250 watt). A solid deposit is produced, which is filtered off after 4 hours. Irradiation continues until chromatography reveals no more educt in the reaction solution. The deposit is dissolved in methylene chloride/methanol=1/1, boiled with active carbon, filtered over diatomaceous earth, and concentrated until crystallisation begins. The filtered, washed, dried crystalline product has a melting point of 295°–295°.

(c)
(5aR*,6aS*,12bS*)-4,5,5a,6,6a,7,8,12b-octahydro-7-methylindolo[4,3-a,b]phenanthridine 8.5 g of lithium aluminium hydride are suspended under a nitrogen atmosphere in 500 ml of diethylether. To this suspension is added whilst stirring a solution of 17.1 g of (5aR*,6aS*,12bS*)-4-benzoyl-4,5,5a,6,6a,7,8,12b-octahydro-8-keto-7-methylindolo[4,3-a,b]phenanthridine in 150 ml of tetrahydrofuran. The temperature of the reaction solution increases to boiling point. The reaction solution is stirred for 2 hours, and subsequently hydrolysed by adding concentrated aqueous sodium hydroxide solution, then mixed with magnesium sulphate and diatomaceous earth, and filtered. The filter cake is suspended in 2N aqueous ammonium hydroxide and re-extracted with ethyl acetate. The combined organic phases are dried over magnesium sulphate, filtered and concentrated. The oil thus obtained is crystallised from ethyl acetate. After filtering, washing and drying, the crystalline product is obtained. It has a melting point of 149°–150°.

(d)
trans-4,6,6a,7,8,12b-hexahydro-7-methylindolo[4,3-ab]-phenanthridine 2 g of (5aR*,6aS*,12bS*)-4,5,5a,6,6a,7,8,12b-octahydro-7-methylindolo[4,3-ab]phenanthridine are dissolved in 250 ml of methylene chloride. 20 g of actively precipitated manganese dioxide are subsequently suspended in the solution, and the suspension obtained is stirred at room temperature until thin-layer chromatography reveals no more educt. The reaction solution is then filtered over diatomaceous earth, concentrated and the resultant oil crystallised from methylene chloride. The crystalline title compound is obtained. It melts at 215°.

The following compounds of formula Ia are produced in analogous manner to example 1 (all racemates):

| Example | $R_1$ | $X_1$ | $X_2$ | $R_{3a}$ | M.P. |
|---|---|---|---|---|---|
| 1a | H | H | H | —CH$_2$—CH$_3$ | 227–229°(2) |
| 1b | H | H | H | —CH$_2$—CH$_2$—CH$_3$ | 224–225°(3) |
| 1c | —CH$_3$ | H | H | —CH$_3$ | 184–185°(1) |
| 1d | H | H | H | —CH$_2$—CH=CH$_2$ | 203°(1) |
| 1e | H | H | H | —CH$_2$-(tetrahydrofuranyl) | 230°(1) |
| 1f | H | H | H | —CH$_2$-(C$_6$H$_4$)-OCH$_3$ | 213°(1) |
| 1g | H | 11-OCH$_3$ | H | —CH$_3$ | 211°(1) |
| 1h | H | 11-OH | H | —CH$_3$ | 207°(1) |
| 1i | H | 10-OCH$_3$ | H | —CH$_3$ | 225°(1) |
| 1j | H | 10-OH | H | —CH$_3$ | 245°(1) |
| 1k | H | 10-CH$_3$ | H | —CH$_3$ | 211°(1) |
| 1l | H | 11-CH$_3$ | H | —CH$_3$ | 212°(1) |
| 1m | H | 10-CF$_3$ | H | —CH$_3$ | 230°(1) |
| 1n | H | 10-CH$_3$ | 12-CH$_3$ | —CH$_3$ | 191°(1) |
| 1o | H | 11-Cl | H | —CH$_3$ | 179°(1) |
| 1p | H | 12-OH | H | —CH$_3$ | 265°(1) |

(1)Base
(2)Hydrogen fumarate
(3)Bis[base]fumarate

Example 2:
(—)-trans-4,6,6a,7,8,12b-hexahydro-7-methylindolo[4,3-ab]phenanthridine (a)
(+)-(5aR*,6aS*,12bS*)-4,5,5a,6,6a,7,8,12b-octahydro-7-methylindolo[4,3-AB]phenanthridine 50 g of (±)-(5aR*,6aS*,12bS*)-4,5,5a,6,6a,7,8,12b-octahydro-7-methylindolo[4,3-ab]phenanthridine are dissolved in 500 ml of ethanol at 70°, together with 27.5 g of (+)-mandelic acid. The solution is left to stand over night at room temperature, and the resultant crystallisate is subsequently filtered off, washed with ethanol/ether=1/1, followed by ether, and dried. The crystallisate thus obtained (m.p. 184°–185°) is dissolved whilst hot in 400 ml of ethanol and left to stand over night in order to crystallise. A second crystallisate is obtained, which is filtered off and washed as the first crystallisate, and dried. The second crystallisate is then converted into the free base form by extraction with 1n aqueous sodium carbonate solution/methylene chloride. This form has an optical rotation of $[\alpha]_D^{20} = +378.0°$ (c=1.0/DMF) and is further processed in this form.

(b)
(—)-trans-4,6,6a,7,8,12b-hexahydro-7-methylindolo[4,3-AB]-phenanthridine (—)-trans-4,6,6a,7,8,12b-hexahydro-7-methylindolo[4,3-ab]phenanthridine is obtained in the manner described in example 1 from (+)-(5aR*,6aS*,12bS*)-4,5,5a,6,6a,7,8,12be B-octahydro-7-methylindolo[4,3-ab]phenanthridine. The compound which is crystallised from methylene chloride/methanol=1 melts at 215°, $[\alpha]_D^{20} = -610.7°$ (c=0.84/DMF).

Example 3:
(+)-trans-4,6,6a,7,8,12b-hexahydro-7-methylindolo[4,3-ab]phenanthridine (a)
(−)-(5aR*,6aS*,12bS*)-4,5,5a,6,6a,7,8,12b-octahydro-7-methylindolo[4,3-ab]phenanthridine Using (−)-mandelic acid and the same starting material as in example 2a), the corresponding (−) form is obtained.

(b)
(+)-trans-4,6,6a,7,8,12b-hexahydro-7-methylindolo[4,3-ab]phenanthride (+)-trans-4,6,6a,7,8,12b-hexahydro-7-methylindolo[4,3-ab]phenanthridine is obtained correspondingly from (−)-(5aR*,6aS*,12bS*)-4,5,5a,6,6a,7,8,12b-octahydro-7methylindolo[4,3-ab]phenanthridine, $[\alpha]_D^{20} = +613.1°$ (c=0.83/DMF).

Example 4:
trans-4,6,6a,7,8,12b-hexahydroindolo[4,3-ab]phenanthridine 38.6 g of cyanogen bromide are dissolved in 400 ml of chloroform. 20 g of trans-4,6,6a,7,8,12b-hexahydro-7-methylindolo[4,3-ab]phenanthridine are added to the solution whilst stirring, followed by 10 g of potassium carbonate. The resultant suspension is stirred overnight at room temperature, then filtered and the filtrate concentrated. The residue of evaporation is dissolved whilst heating in 400 ml of concentrated acetic acid, and then 55 ml of water, followed by 47.5 g of zinc powder, are added. The resultant suspension is stirred for 18 hours at 90°. The reaction solution is then filtered, the residue of filtration washed with methylene chloride/methanol, and the combined filtrates evaporated. The residue of evaporation is taken up in methylene chloride/methanol=9/1, and extracted with 1n aqueous sodium carbonate solution. The combined organic phases are washed with sodium chloride solution, dried over magnesium sulphate, filtered, concentrated and the residue chromatographed on silica gel, using methylene chloride/methanol=95/5 (CH₂Cl₂ 10% saturated with NH₃). The title compound is obtained. When crystallised from methanol, its hydrochloride melts at 301°-303°.

The following compounds of formula Ib are produced in analogous manner to example 4:

| Example | R₂ | X₁ | X₂ | Racemate/antipode | M.P. |
|---|---|---|---|---|---|
| 4a | H | 11-OCH₃ | H | Racemate | 283°[1] |
| 4b | H | H | H | (−)* | 311-313°[2] |

[1] Base
[2] Hydrochloride
*$[\alpha]_D^{20} = -436.8°$ (c = 0.7/DMF)

Example 5:
trans-4,6,6a,7,8,12b-hexahydro-4,7-dimethylindolo[4,3-ab]phenanthridine 3 g of trans-4,6,6a,7,8,12b-hexahydro-7-methylindolo[4,3-ab]phenanthridine are dissolved in 60 ml of dimethylformamide. The solution is cooled to −25°, and mixed whilst stirring with 280 mg of a 55% sodium hydride dispersion. The resultant suspension is allowed to warm to 0° over the course of 40 mins., and then 0.81 ml of methyl iodide, dissolved in 10 ml of dimethylformamide, are added in drops. The black reaction solution is stirred for a further 1 hour at 0°, and the dimethylformamide is subsequently removed under a high vacuum. The residue of evaporation is taken up in methylene chloride/methanol=95/5, extracted with water, and the combined organic phases dried, filtered and concentrated. The residue of evaporation is chromatographed on silica gel with methylene chloride/methanol=98/2 (methylene chloride 10% saturated with NH₃). The title compound which crystallises from the solvent mixture used for chromatography is thus obtained. After washing with ether and subsequent drying, it melts at 184°-185°.

Example 6:
trans-5-bromo-4,6,6a,7,8,12b-hexahydro-7-methyl indolo[4,3-ab]phenanthridine 4 g of trans-4,6,6a,7,8,12b-hexahydro-7-methylindolo[4,3-ab]phenanthridine are suspended in 300 ml of chloroform, and the stirred suspension is heated to reflux temperature. A solution of 2.7 g of bromosuccinimide in 100 ml of chloroform is quickly added, and the clear reaction solution is then refluxed for a further hour. The cooled reaction solution is extracted with 1n aqueous sodium carbonate solution, the organic phases dried, concentrated and the evaporation residue chromatographed on silica gel with methylene chloride/methanol=95/5 (methylene chloride 10% saturated with NH₃). The title compound is obtained. Its bis[base]fumarate is crystallised from methanol (m.p. 235°-237°).

The following compounds of formula Id are produced in analogous manner to those disclosed for the production of 2-substituted ergoline derivatives, from the corresponding compounds of formula Ia:

| Example | R₁ | R₂ₐ | R₃ₐ | X₁ | X₂ | Racemate/antipode | M.P. |
|---|---|---|---|---|---|---|---|
| 6a | H | Cl | —CH₃ | H | H | Racemate | 239-240°[2] |
| 6b | H | —CH₃ | —CH₃ | H | H | Racemate | 201-204°[1] |
| 6c | H | Br | —CH₃ | H | H | (−)* | 235-237°[1] |
| 6d | H | —CH₃ | —CH₃ | H | H | (−)** | 226-229°[1] |

[1] Base
[2] Bis[base]fumarate
*$[\alpha]_D^{20} = -550.8°$ (c = 1.1/DMF)
**$[\alpha]_D^{20} = -587.8°$ (c = 0.64/DMF)

What we claim is:
1. A compound of formula I

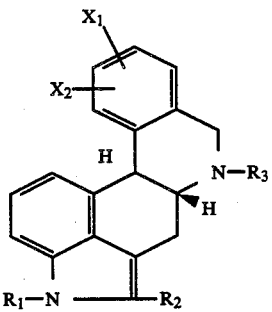

wherein
R₁ and R₃ independently are hydrogen, (C₁₋₄)alkyl, (C₃₋₅)alkenyl wherein the double bond is not adjacent to the nitrogen atom, (C$_{3-6}$)cycloalkyl(C$_{1-3}$)alkyl, phenyl(C$_{1-3}$)alkyl optionally substituted in the phenyl ring by (C$_{1-4}$)alkyl, (C$_{1-4}$)alkoxy, hydroxy or halogen, or 2- or 3-furyl(C$_{1-3}$)alkyl, R$_2$ is hydrogen, chlorine, bromine or methyl, X$_1$ and X$_2$ independently are hydrogen, (C$_{1-4}$)alkyl, (C$_{1-4}$)alkoxy, hydroxy, halogen or trifluoromethyl, in free base or acid addition salt form.

2. A compound of claim 1 wherein

R$_1$ and R$_3$ independently are hydrogen, (C$_{1-4}$)alkyl, (C$_{3-5}$)alkenyl wherein the double bond is not adjacent to the nitrogen atom, (C$_{3-6}$)cycloalkyy (C$_{1-3}$)alkyl, phenyl(C$_{1-3}$)alkyl optionally monosubstituted by methyl, methoxy, hydroxy or halogen, or 2- or 3-furyl(C$_{1-3}$)alkyl, R$_2$ is hydrogen, chlorine, bromine or methyl, X$_1$ and X$_2$ independently are hydrogen, (C$_{1-4}$)alkyl, (C$_{1-4}$)alkoxy, hydroxy, halogen or trifluormethyl.

3. A compound of claim 1 wherein

R$_1$ is hydrogen or (C$_{1-4}$)alkyl,

R$_2$ is hydrogen, chlorine, bromine or methyl,

R$_3$ is hydrogen, (C$_{1-4}$)alkyl, benzyl optionally monosubstituted by (C$_{1-4}$)alkoxy, or 2-furylmethyl, X$_1$ is in position 10, 11 or 12 and is hydrogen, (C$_{1-4}$)alkyl, (C$_{1-4}$)alkoxy, hydroxy, halogen or trifluoromethyl and X$_2$ is hydrogen.

4. A compound of claim 1 wherein R$_1$, R$_2$, X$_1$ and X$_2$ are hydrogen and R$_3$ is methyl, in form of the (−)-isomer.

5. A pharmaceutical composition useful in the treatment of Parkinson's disease, conjective cardiac insufficiency, hypertension, renal failure with reduced urine excretion or pain comprising a therapeutically effective amount of a compound according to claim 1 in pharmaceutically acceptable form, in association with a pharmaceutical carrier or diluent.

6. A method of treating a subject suffering from Parkinson's disease, congestive cardiac insufficiency, hypertension, renal failure with reduced urine excretion or pain, which comprises administering a therapeutically effective amount of a compound of claim 1 in pharmaceutically acceptable form.

7. The compound of claim 1, which is trans-4,6,6a,7,8,12b-hexahydro-7-methyl-indolo[4,3-ab] phenanthridine.

8. A compound of claim 1 in which R$_2$ is hydrogen and R$_1$, X$_1$, X$_2$, and R$_3$ are respectively:

| | | | | |
|---|---|---|---|---|
| (a) | H | H | H | —CH$_2$—CH$_3$ |
| (b) | H | H | H | —CH$_2$—CH$_2$—CH$_3$ |
| (c) | —CH$_3$ | H | H | —CH$_3$ |
| (d) | H | H | H | —CH$_2$—CH=CH$_2$ |
| (e) | H | H | H |  |
| (f) | H | H | H |  |

9. A compound of claim 1 in which R$_2$ is hydrogen and R$_1$, X$_1$, X$_2$ and R$_3$ are respectively:

| | | | | |
|---|---|---|---|---|
| (g) | H | 11-OCH$_3$ | H | —CH$_3$ |
| (h) | H | 11-OH | H | —CH$_3$ |
| (i) | H | 10-OCH$_3$ | H | —CH$_3$ |
| (j) | H | 10-OH | H | —CH$_3$ |
| (k) | H | 10-CH$_3$ | H | —CH$_3$ |
| (l) | H | 11-CH$_3$ | H | —CH$_3$ |
| (m) | H | 10-CF$_3$ | H | —CH$_3$ |
| (n) | H | 10-OCH$_3$ | 12-CH$_3$ | —CH$_3$ |
| (o) | H | 11-Cl | H | —CH$_3$ |
| (p) | H | 12-OH | H | —CH$_3$ |

10. The compound of claim 1 which is (+)-trans-4,6,6a,7,8,12b-hexahydro-7-methyl-indolo[4,3-ab]phenanthridine.

11. The compound of claim 1 which is trans-4,6,6a,7,8,12b-hexahydroindolo[4,3-ab]-phenanthridine.

12. The compound of claim 1 in which R$_1$ is hydrogen R$_2$, X$_1$, x$_2$ and R$_3$ are H,11-OCH$_3$, H, and H in racemate form.

13. The compound of claim 1 in which R$_1$ is hydrogen and R$_2$, X$_1$, X$_2$ and R$_3$ are H, H, H, and H in (−) isomer form.

14. The compound of claim 1 which is trans-4,6,6a,7,8,12b-hexahydro-4,7-dimethyl-indolo[4,3-ab]phenanthridine.

15. The compound of claim 1 in which trans-5-bromo-4,6,6a,7,8,12b-hexahydro-7-methyl-indolo[4,3-ab]phenanthridine.

16. The compound of claim 1 in racemate form in which R$_1$, R$_2$, R$_3$, X$_1$ and X$_2$ are respectively:

| | | | | |
|---|---|---|---|---|
| (a) | H | Cl | —CH$_3$ | H | H |
| (b) | H | —CH$_3$ | —CH$_3$ | H | H |

17. The compound of claim 1 in (−) isomer form in which R$_1$, R$_2$, R$_3$, X$_1$ and X$_2$ are respectively:

| | | | | |
|---|---|---|---|---|
| (c) | H | Br | —CH$_3$ | H | H |
| (d) | H | —CH$_3$ | —CH$_3$ | H | H |

* * * * *